United States Patent [19]
Farra et al.

[11] Patent Number: 5,746,719
[45] Date of Patent: May 5, 1998

[54] FLUID FLOW CONTROL SYSTEM INCORPORATING A DISPOSABLE PUMP CARTRIDGE

[75] Inventors: Robert Farra, Acton; Ronald J. Forni, Littleton, both of Mass.

[73] Assignee: Arthur D. Little, Inc., Cambridge, Mass.

[21] Appl. No.: 736,879

[22] Filed: Oct. 25, 1996

[51] Int. Cl.$^6$ .................................................. A61M 1/00
[52] U.S. Cl. ................ 604/151; 604/131; 128/DIG. 12; 418/56
[58] Field of Search ................... 604/151, 131, 604/153, 65, 118, 119; 128/DIG. 12; 418/56

[56] References Cited

U.S. PATENT DOCUMENTS

| | | |
|---|---|---|
| 3,572,319 | 3/1971 | Bittner et al. |
| 4,429,693 | 2/1984 | Blake et al. ................ 604/119 X |
| 4,617,013 | 10/1986 | Betz ................ 604/119 X |
| 4,731,000 | 3/1988 | Haag ................ 418/56 X |
| 4,798,580 | 1/1989 | DeMeo et al. ................ 604/119 |
| 4,875,839 | 10/1989 | Sakata et al. ................ 418/56 X |
| 4,950,235 | 8/1990 | Slate et al. ................ 604/65 |
| 5,131,827 | 7/1992 | Tasaka ................ 418/56 X |
| 5,464,391 | 11/1995 | DeVale . |
| 5,499,969 | 3/1996 | Beuchat et al. ................ 604/151 X |

OTHER PUBLICATIONS

Stortz Publication, "Fluid Dynamics, A Primer" (1994).
Stortz Publication, "Fluidics: The Clinical Perspective" (1994).

*Primary Examiner*—Sam Rimell
*Assistant Examiner*—Luke Yeh

[57] ABSTRACT

A fluid flow control system includes a disposable cartridge which is receivable in a shifting carrier body portion of a control module. The disposable cartridge houses a disposable pump and a pressure transducer element which are fluidly interconnected by an internal fluid flow circuit formed in part by an elastomeric separating sheet within the cartridge. Following loading of the cartridge, shifting of the carrier body portion automatically results in a drive connection to the pump, the positioning of various flow control valves within the cartridge and the seating of the pressure transducer element to the control module. External flow lines are readily placed in fluid communication with the internal fluid flow circuit through exterior connection ports provided on the cartridge.

46 Claims, 8 Drawing Sheets

FLUID FLOW CONTROL SYSTEM INCORPORATING A DISPOSABLE PUMP CARTRIDGE

BACKGROUND OF THE INVENTION

1. Field of the Invention

The present invention pertains to the fluid pumping art and, more specifically, to a fluid flow system incorporating a control module to which is removably attached a disposable pump cartridge that defines an internal fluid flow circuit. The system is particularly applicable for use in a surgical procedure requiring a controlled pressure and/or flow rate of a fluid either delivered to or withdrawn from a patient, thereby exposing the fluid flow circuit to possible contaminants.

2. Discussion of the Prior Art

In some environments, pumping devices are required that need only produce rather low flow rates but which cannot be reused without being thoroughly cleaned between uses. For example, during a surgical or other medical procedure, various bodily fluids may need to be delivered to and withdrawn from a patient. A pumping device used for this purpose will obviously be exposed to these fluids. Following the procedure, the pumping device and other exposed system components will either have to be discarded or, in some way, sanitized prior to subsequent use. Although the associated pumping rates for these systems are rather low such that the pumping devices can be made fairly small, the cost associated with manufacturing these pumping devices and other exposed system components is still quite high and therefore disposing of such these components following a single use would be quite costly. Of course, cleaning and sterilizing these components for later use can also be costly, as well as time consuming.

Some fluid flow control systems also must provide for the flow of numerous fluids. For example, during eye surgery, it is common to supply an irrigation fluid to the surgical site while withdrawing or aspirating additional, fluid suspended material from the site. During such a procedure, it is imperative to properly control the flow of fluids to maintain a proper intraocular environment. Major fluctuations in intraocular pressure can occur if a proper fluid balance is not maintained during irrigation and aspiration, either alone or during a phacoemulsification procedure. Perhaps most important is aspiration control as this is responsible for maintaining the shape of the anterior chamber throughout the surgery. Various pumping systems, including peristaltic and venturi-based systems, are commonly used in the art to perform such eye operations. In any event, controlling the flow rate and/or pressure from the surgical site is critical. Although the surgeon generally controls the system, typically through a foot pedal unit, additional sensory equipment is being more commonly provided to regulate system flow rates and/or pressures. Of course, this sensory equipment further adds to the cost of such systems and potentially adds to the number of components that must be sanitized between uses.

Although some fluid flow control systems have been proposed for use in medical environments wherein the systems incorporate pumping devices that are designed to be discarded following a single use, such known systems fail to address all the needs in the art. For instance, such known systems lack disposable portions which efficiently provide for the flow of multiple fluids there through, fail to present designs directed to minimizing costs associated with system production and use so as to present an economically viable system, do not define versatile arrangements which can accurately and selectively control both fluid flow rates and pressures, and are not simple in construction and operation, yet reliable, so as to gain wide acceptance in the marketplace. Therefore, there exists a need in the art for an improved fluid flow control system which overcomes these and other problems known in the art.

SUMMARY OF THE INVENTION

A versatile and cost effective fluid flow control system is provided which is particularly adapted for use in environments requiring rather low flow rates (generally less than 60 ml/min) and which will have portions that will be exposed to potential contaminants. The fluid flow control system includes a disposable cartridge defined by a housing within which is mounted a pump and a pressure transducer element. The cartridge housing has numerous external connection ports for attaching tubes from a fluid supply source, an output fluid conduit, a contaminated fluid intake line and a reservoir. A separating member in the form of an elastomeric sheet is positioned in the cartridge housing and defines, along with open channels formed on an inner surface of one section of the cartridge housing, a plurality of flow passages which collectively define a fluid flow circuit that is in fluid communication with each of the external connection ports, as well as inlet and outlet ports for each of the pump and pressure transducer element.

The fluid flow control system also includes a control module for supporting the disposable cartridge during system operation and for regulating fluid flow through the fluid flow circuit. The control module includes a control housing having a main body portion and a carrier body portion that is shiftable, through a mechanism carried by the main body portion, relative to the main body portion between a cartridge loading/unloading position and a system in-use position. The control module incorporates a plurality of linearly shifting valve members, a reusable transducer element and a pump driveshaft that are automatically interengaged with portions of the disposable cartridge following loading and shifting of the carrier body portion.

In accordance with the invention, the disposable cartridge contains, or has fluidly connected thereto, all of the system components which can become contaminated during use. A system user need only place a new cartridge in the carrier body portion to cause the cartridge to be operatively interconnected to the control module and then connect the required tubes or conduits to the external connection ports. Flow within and through the cartridge will be regulated by the extension and retraction of the valve members which can engage the elastomeric sheet and, in combination with the cartridge housing, pinch the sheet to cause flow regulation at selected points in the fluid flow circuit. In the preferred embodiment, flow through the system can be selectively controlled based on operator inputs and selected parameters of system pressure, flow rate or both.

Additional features and advantages of the invention will become more readily apparent from the following detailed description of a preferred embodiment thereof when taken in conjunction with the drawings wherein like reference numerals refer to corresponding parts in the several views.

DETAILED DESCRIPTION OF THE PREFERRED EMBODIMENT

For purposes of this description, the fluid flow control system of the invention will be particularly described in connection with a fluid circuit designed for both irrigating and aspirating a surgical site. With initial reference to FIG. 1, such an overall fluid flow circuit that can be utilized in connection with surgical procedures of the eye is generally indicated at 2. Fluid flow circuit 2 includes a first tubular passageway 4 that is adapted to receive a supply of irrigation fluid, such as saline, that is received within first tubular passageway 4 through a supply inlet zone 6. First tubular passageway 4 terminates in a discharge nozzle 8, the position of which is controlled by a surgeon or other operating attendant for irrigation purposes. Between supply inlet zone 6 and discharge nozzle 8, a first valve control point 10 is defined. As will be described more fully below, first valve control point 10 establishes a predetermined location within first tubular passageway 4 where the flow of fluid therethrough can be controlled.

Figures 1, 7:
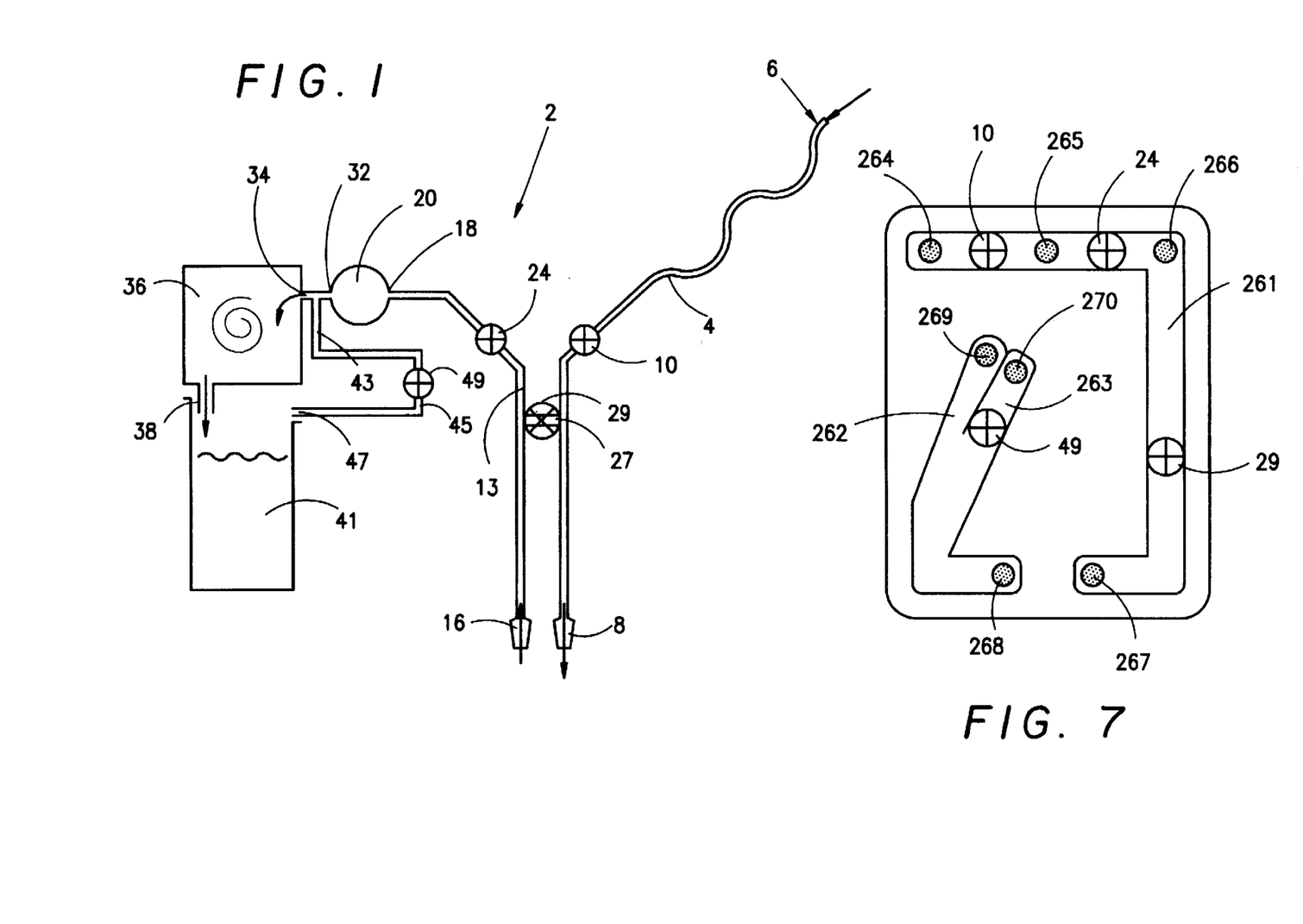
FIG. 1 is an overall schematic view of a fluid flow circuit established by a preferred embodiment of the invention.
FIG. 7 is a schematic of a fluid flow circuit formed within the cartridge of FIG. 2.

Fluid flow circuit 2 also includes a second tubular passageway 13 including an intake nozzle 16 at one end thereof. In flow circuit 2, intake nozzle 16 and second tubular passageway 13 are used for aspiration purposes. Remote from intake nozzle 16, second tubular passageway 13 is attached to an inlet port 18 of a pressure transducer 20. Along second tubular passageway 13 is defined a second valve control point 24. Second tubular passageway 13 may be interconnected through a vent line 27 to first tubular passageway 4. As represented in this Figure, vent line 27, if provided, would have associated therewith a third valve control point 29.

Pressure transducer 20 has an outlet 32 that is connected to an inlet port 34 of a pump 36. As will be described more fully below, pump 36 can be constituted by numerous types of known pumping units, however, in the preferred embodiment, pump 36 is constituted by a miniature scroll fluid device having an output flow rate ranging in the order of 1 ml/min to 60 ml/min, at a maximum vacuum pressure of approximately 550 mm Hg. More specifically, the preferred embodiment incorporates a scroll fluid device as set forth in a co-pending U.S. Patent Application entitled "Compact Scroll Fluid Device", filed on the same date herewith in the name of Ronald J. Forni. In a similar manner, pressure transducer 20 can take various forms in accordance with the present invention but is preferably constructed in the manner set forth in co-pending U.S. Patent Application entitled "Fluid Pressure Sensing Unit" filed on the same date herewith in the names of Reed and Franzosa. Although the particular configuration of pressure transducer 20 and pump 32 are not considered part of the present invention, the descriptions in the two cited co-pending applications are hereby incorporated by reference for the sake of completeness.

Pump 36 has associated therewith a discharge port 38 that is in fluid communication with a reservoir 41. Outlet 32 of pressure transducer 20 is also connected to a first end 43 of a calibration conduit 45. Calibration conduit 45 includes a second end 47 that also discharges into reservoir 41. Located within calibration conduit 45, between first and second ends 43 and 47, is a normally closed pressure calibration valve indicated at 49. Calibration conduit 45 and its associated valve 49 are merely included for the sake of completeness and can be used to calibrate pressure transducer 20, however, since this is not considered an essential feature of the present invention as pressure transducer 20 may not require such calibration.

A major aspect of the present invention concerns integrating the structural components of fluid flow circuit 2 into an assembly that can be made in a compact and economically viable manner. Since the components of fluid flow circuit 2 represent all of the structure that will be subjected to potentially contaminated fluids during the surgical operation, incorporating these components into an integrated assembly will not only enable the components to be readily isolated from other system components which need not be directly exposed to the various fluids flowing through circuit 2, but can provide for the efficient replacement of a used assembly and disposal thereof following a single use as will become more fully apparent below.

Reference will now be made to FIGS. 2–6 in describing the structure of a disposal cartridge 52 designed to integrate the components of fluid flow circuit 2. Disposable cartridge 52 includes a first housing section 54 and a second housing section 56 that are adapted to be attached together along a circumferential joint 58. In the preferred embodiment, first and second housing sections 54 and 56 are molded of plastic and are joined at joint 58 through a welding operation. Of course, other attachment arrangements, including mechanical fasteners or adhesive could be utilized.

Figure 4:
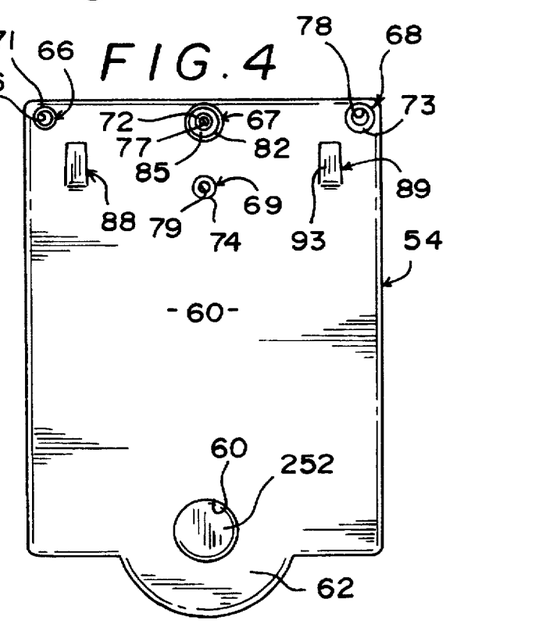
FIG. 4 is a front plan view of the cartridge of FIG. 2.
Figure 6:
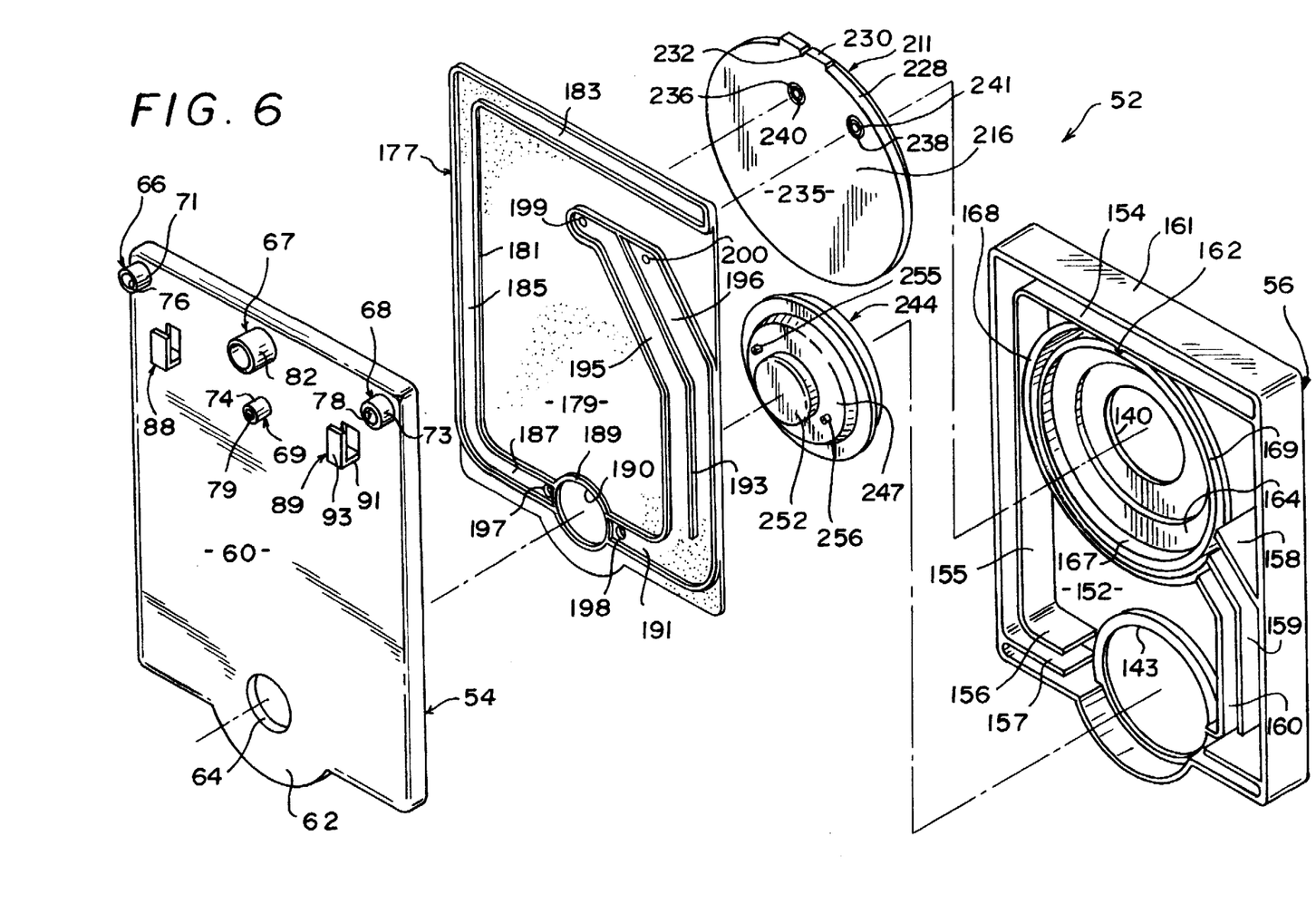
FIG. 6 is an exploded view of the cartridge of FIG. 2, similar to that shown in FIG. 5 but taken in an opposite direction.

As best shown in FIGS. 4 and 6, first housing section 54 includes an outer surface 60 that is generally rectangular in shape but which is provided with a semi-circular lower extension 62. Spaced from semi-circular lower extension 62, outer surface 60 of first housing section 54 is formed with a bore 64 and, formed at a top section of first housing 54 are first, second, third and fourth external connection ports 66–69. In the preferred embodiment, each external connection port 66–69 is defined by a respective upstanding, generally cylindrical member 71–75 having a central bore 76–79. External connection ports 66–69 are adapted to be interconnected to tubes or other fluid conduits (not shown) that are interconnected to disposal cartridge 52 to complete fluid flow circuit 2. To assure the proper connections by preventing potential human error in completing the circuit, in the preferred embodiment, external connection ports 66–69 have different sizes which correspond to the sizes of the respective conduits to be attached thereto.

Second external connection port 67 is actually defined by cylindrical member 72 which constitutes an inner cylindrical member and an outer cylindrical member 82 which are spaced by an annular gap 85 as clearly shown in FIG. 4. Each of external connection ports 66, 68 and 69 are adapted to have tubular conduits fit about their respective cylindrical members 71, 73 and 74 while a conduit is adapted to be inserted within annular gap 85 and about inner cylindrical member 72 of second external connection port 67 to be placed in fluid communication with central bore 77. Finally, outer surface 60 is also formed with a pair of spaced suspension members 88 and 89 which, as will be more fully discussed below, are provided for suspending a pouch or other container (not shown) that defines reservoir 41 from disposable cartridge 52. In the preferred embodiment, suspension members 88 and 89 each includes an outwardly projecting portion 91 and an upstanding tab portion 93. When a tubular pouch is utilized for reservoir 41, the pouch is preferably provided with spaced apertures for use in hanging the pouch from suspension members 88 and 89.

Figure 5:
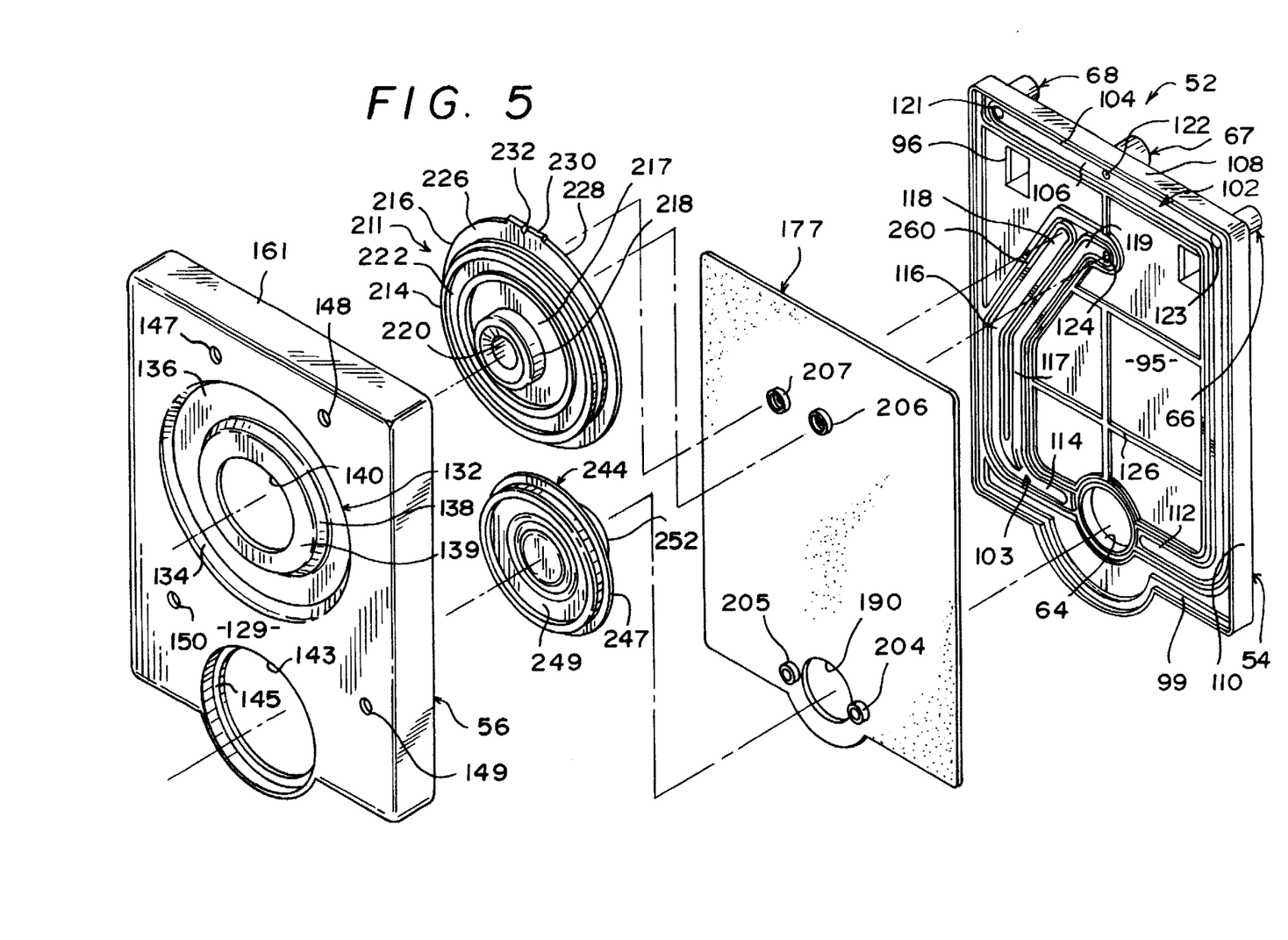
FIG. 5 is an exploded view of the cartridge of FIG. 2 taken in a first direction.

First housing section 54 has an inner surface 95 as best shown in FIG. 5. Inner surface 95 is formed with a pair of boxed-shaped openings 96 at suspension members 88 and 89, an inner annular ledge 99 which extends about the entire inner periphery of first housing section 54 and a plurality of open channels generally indicated at 102 and 103. Channels 102 and 103 are actually defined by raised wall portions 104 of inner surface 95. As shown, open channel 102 includes a first end 106 that extends along a top wall portion 108 of first housing section 54, downward along side wall portion 110 and then terminates at a second end 112 adjacent bore 64. Open channel 103 has a first end 114 arranged adjacent bore 64 and is thereafter divided into subchannels 116 and 117 having respective terminal ends 118 and 119. As clearly shown in this figure, open channel 102 is formed with first, second and third holes 121–123 at top wall portion 108 and open channel 103 is formed with a fourth hole 124 at terminal end 119. Holes 121–124 are actually defined by central bores 76–79 of external connection ports 66–69 and therefore channels 102 and 103 are open external to disposable cartridge 52. Finally, inner surface 95 of first housing section 54 is preferably provided with a plurality of reinforcing ribs, one of which is indicated at 126.

Figure 2:
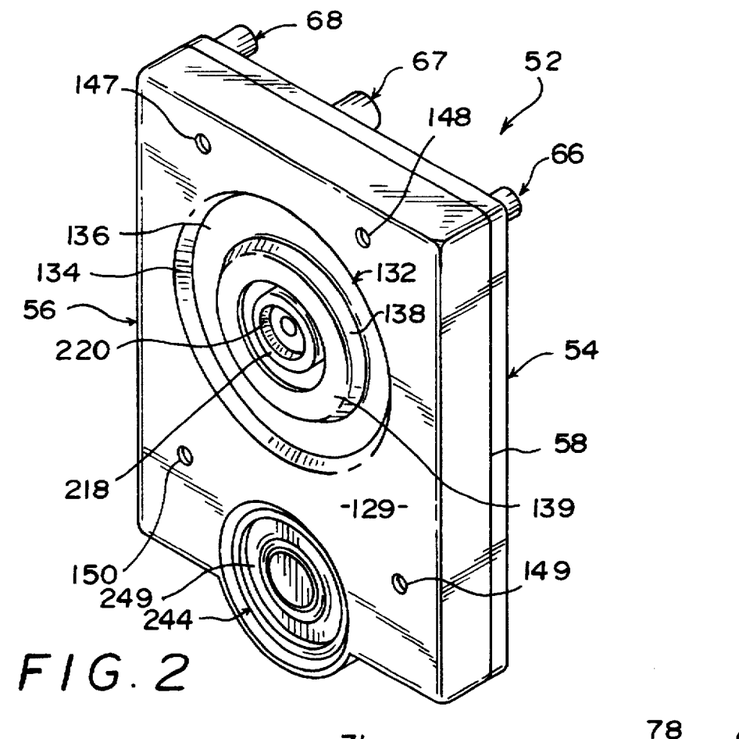
FIG. 2 is a perspective view of a disposable cartridge constructed in accordance with the invention.
Figure 3:
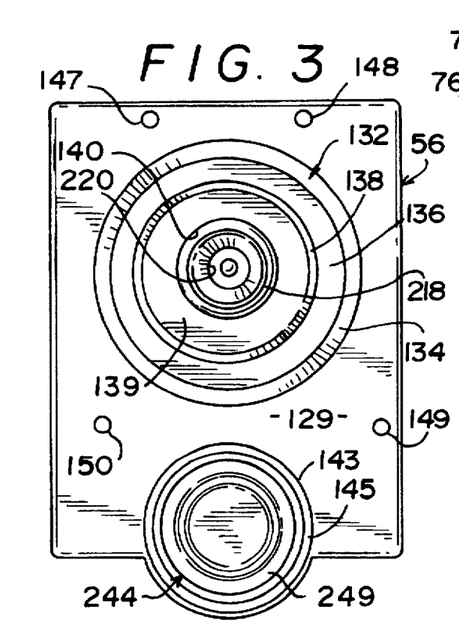
FIG. 3 is a rear plan view of the cartridge of FIG. 2.

With particular reference to FIGS. 2, 3 and 5, second housing section 56 includes an outer surface 129 having an upper recessed section 132 defined by an inwardly tapering, annular wall 134 that leads to a base 136. Radially inwardly of base 136 is an upwardly extending and inwardly tapering wall 138 that leads to a central annular ledge 139 that is provided with an opening 140. Spaced below recessed section 132, second housing 56 is provided with a lower opening 143 that defines an inner, annular seating surface 145. Outer surface 129 is further provided with various spaced apertures 147–150 that extend entirely through second housing section 56.

As shown in FIG. 6, second housing section 56 has an inner surface 152 from which project numerous upstanding interior wall members 154–160. Upstanding interior wall members 154–156 perform structural integrity and valve member guiding functions as will become more clearly evident hereinafter when considered in connection with the type of valving incorporated in the preferred embodiment. At this point, however, it should be realized that apertures 147 and 148 are located between a top wall 161 of second housing section 56 and wall member 154, aperture 149 is arranged between a side wall (not labeled) of second housing section 56 and wall member 155, and aperture 150 is positioned between an opposing side wall (not labeled) of second housing section 56 and wall member 159. Upstanding interior wall member 154 is preferably formed with a depending detent member 162 which, as will be described more fully below, provides an alignment and mounting aid for pump 36. Within second housing section 56, base 136 of recessed section 132 defines a raised surface 164 from which extends an annular wall 167 having an upper rim 168 that is formed with a groove 169. Groove 169 is adapted to receive an O-ring (not shown) for use in sealing against a portion of pump 36.

Mounted between first and second housing sections 54 and 56 is an elastomeric sheet 177 which is best shown in FIGS. 5 and 6. Elastomeric sheet 177 is extremely flexible and pliable and includes a first side 179 formed with numerous upstanding sealing walls 181 which are adapted to be sealingly mated with the raised wall portions 104 of channels 102 and 103 to define plural fluid flow passages. More specifically, upstanding sealing walls 181 of elastomeric sheet 177 defines an upper channel 183 that leads to a side channel 185 and a bottom channel portion 187. Bottom channel portion 187 terminates at a wall 189 formed about an opening 190. In addition, upstanding sealing walls 181 defines a further bottom channel portion 191 that is bifricated by means of an upstanding wall 193 into subchannel portions 195 and 196.

Elastomeric sheet 177 is also provided with a plurality of through holes 197–200. More specifically, a first through hole 197 is provided in bottom channel portion 187 adjacent terminal wall 189, a second through hole 198 is provided in bottom channel portion 191 adjacent wall 189, and third and fourth through holes 199 and 200 are provided at terminal ends of subchannel portions 195 and 196 respectively. On the second side 201 of elastomeric sheet 177, each of through holes 197–200 has associated therewith upstanding sealing rings 204–207 respectively.

As indicated above, pump 36 is preferably constitued by a scroll fluid device that is generally indicated in these figures at 211. Although the particular construction of scroll fluid device 211 is not considered part of the present invention as various other types of known pumps could also be utilized, in general, scroll fluid device 211 includes a pair of meshing scroll elements 214 and 216. Although not shown, first and second scroll elements 214 and 216 have internally meshed involute spiral wrap members that define at least one fluid chamber that moves radially from a pump inlet zone to a pump outlet zone when one of the wrap members is orbited along a circular path about an orbit center relative to the other of the wrap members. In accordance with the preferred construction of scroll fluid device 211 as it pertains to the assembly of disposable cartridge 52, first scroll element 214 includes an exposed side 217 that is formed with a central hub 218 provided with a bore 220. In addition, exposed side 217 is formed with an annular groove 222 that is adapted to receive an O-ring or another known type of seal (not shown) used to fluidly seal first scroll element 214 to first housing section 54 as will be detailed below. Second scroll element 216 includes a flange 226 that extends radially outwardly of first scroll element 214. Flange 226 includes a peripheral edge 228 that is formed with an upstanding ledge 230 having a central notch 232. As best shown in FIG. 6, second scroll element 216 has an exposed side 235 that is formed with a pair of spaced annular recesses 236 and 238 that define central upstanding connectors 240 and 241. Upstanding connectors 240 and 241 actually define outlet and inlet ports for scroll fluid device 211.

Also positioned within disposable cartridge 52 is a disposable pressure transducer element 244 that actually constitutes part of an overall pressure transducer assembly preferably constructed in the manner set forth in accordance with the above-identified and incorporated by reference co-pending U.S. Patent Application. As shown, pressure transducer element 244 includes an outer shell 247 preferably formed of plastic to which is sealed a deflectable diaphragm 249 that is preferably formed of stainless steel. Shell 247 is formed with a central locating projection 252, as well as a pair of diametrically opposed fluid flow connectors 255 and 256 which constitute inlet and outlet ports for pressure transducer 244 to enable the flow of system fluid therethrough.

As represented in FIGS. 2-6, first and second housing sections 54 and 56 of disposable cartridge 52 are adapted to be interconnected with elastomeric sheet 177, scroll fluid device 211 and pressure transducer element 244 disposed therein. More specifically, elastomeric sheet 177 is preferably adhesively secured to inner surface 95 of first housing section 54 such that elastomeric sheet 177 sealingly extends across open channels 102 and 103 such that these channels define sealed fluid flow passages open only at holes 121-124 and through holes 197-200. More specifically, upstanding sealing walls 181 of elastomeric sheet 177 are actually received within a continuous groove 260 formed about open channels 102 and 103. Scroll fluid device 211 is positioned within second housing section 56 with annular groove 222 being seated upon raised surface 164 and central hub 218 projecting into opening 140. Central hub 218 has a smaller diameter than opening 140 to permit the unobstructed orbital movement of first scroll element 214 during operation of scroll fluid device 211. Second scroll element 216 is also seated within second housing section 56 with flange 226 being sealed thereto by means of the O-ring positioned within groove 169 and upstanding ledge generally abutting upstanding interior wall member 154. Furthermore, notch 232 provided on second scroll element 216 receives detent member 162 to aid in the aligning and mounting of scroll fluid device 211. Pressure transducer 244 is positioned in lower opening 143 with diaphragm 249 being exposed at outer surface 129 of second housing section 56. In addition, connectors 255 and 256 of pressure transducer element 244 are mated with upstanding sealing rings 204 and 205 of elastomeric sheet 177 while central locating projection 252 extends through opening 190 and into bore 64. Also, upstanding sealing rings 206 and 207 of elastomeric sheet 177 are interconnected with central upstanding connectors 240 and 241 of scroll fluid device 211.

From the above description, it should be readily apparent that scroll fluid device 211 is sealingly mounted within disposable cartridge 52 and has one port (an inlet port in the preferred embodiment disclosed) fluidly connected with the flow passage defined by the combination of open subchannel 118 and elastomeric sheet 177 through the use of the upstanding sealing ring 207. In a similar manner, connector 240 which defines an outlet for scroll fluid device 211 is connected through upstanding sealing ring 206 to subchannel 117 at fourth hole 124. Again, fourth hole 124 leads to connection port 69. As indicated above, a reservoir 41 in the form of a pouch is adapted to be suspended from suspension members 88 and is connected to port 69 such that the output from scroll fluid device 211 leads to reservoir 41. The inlet and outlet of pressure transducer element 244 are also in fluid communication with the fluid passages defined by open channels 102 and 103 and elastomeric sheet 177 through connectors 255 and 256 and first and second through holes 197 and 198. Upstanding sealing rings 204 and 205 provide for a complete seal in this fluid communication.

Therefore, once assembled, the disposable cartridge establishes the overall fluid flow circuit generally indicated at 2 in FIG. 1. This is perhaps best represented schematically in FIG. 7 wherein at least fluid passages 261-263 are established with fluid passage 261 receiving a supply of fluid (for irrigation purposes in the embodiment disclosed) at point 264; an outlet supply of irrigating fluid is provided at 265; an input flow of aspirated fluid (perhaps with suspended particles therein) is placed in fluid communication with flow passage 261 at reference numeral 266; fluid is permitted to flow to pressure transducer element 244 from fluid passage 261 at location 267; flow exits pressure transducer element 244 at location 268; inlet fluid to scroll fluid device 211 occurs at point 269 and point 270 represents an output to reservoir 41. First, second and third valve control points 10, 24 and 29, as well as a valve point for calibration valve 49, is also indicated. As will be discussed more fully below, these valve point locations represent zones wherein elastomeric sheet 177 is pinched such that it extends within a respective portion of fluid flow passages 261 and 263 to selectively control the flow of fluid through these passages. Since elastomeric sheet 177 is formed of a flexible and pliable material, the sheet material itself is actually utilized to perform the valving function, in combination with valve elements used to deflect the sheet as will be more fully described below. In any event, at this point, it should be readily apparent that disposable cartridge 52 provides for an integrated assembly of components, as well as an internal fluid flow circuit to which only a few fluid flow connections need be made at connection ports 66-69 to complete the overall circuit. It should also be evident that these external connection ports 66-69 directly correspond to the tube attaching locations discussed above with reference to numbers 264, 265, 266 and 270 respectively.

Figure 8:
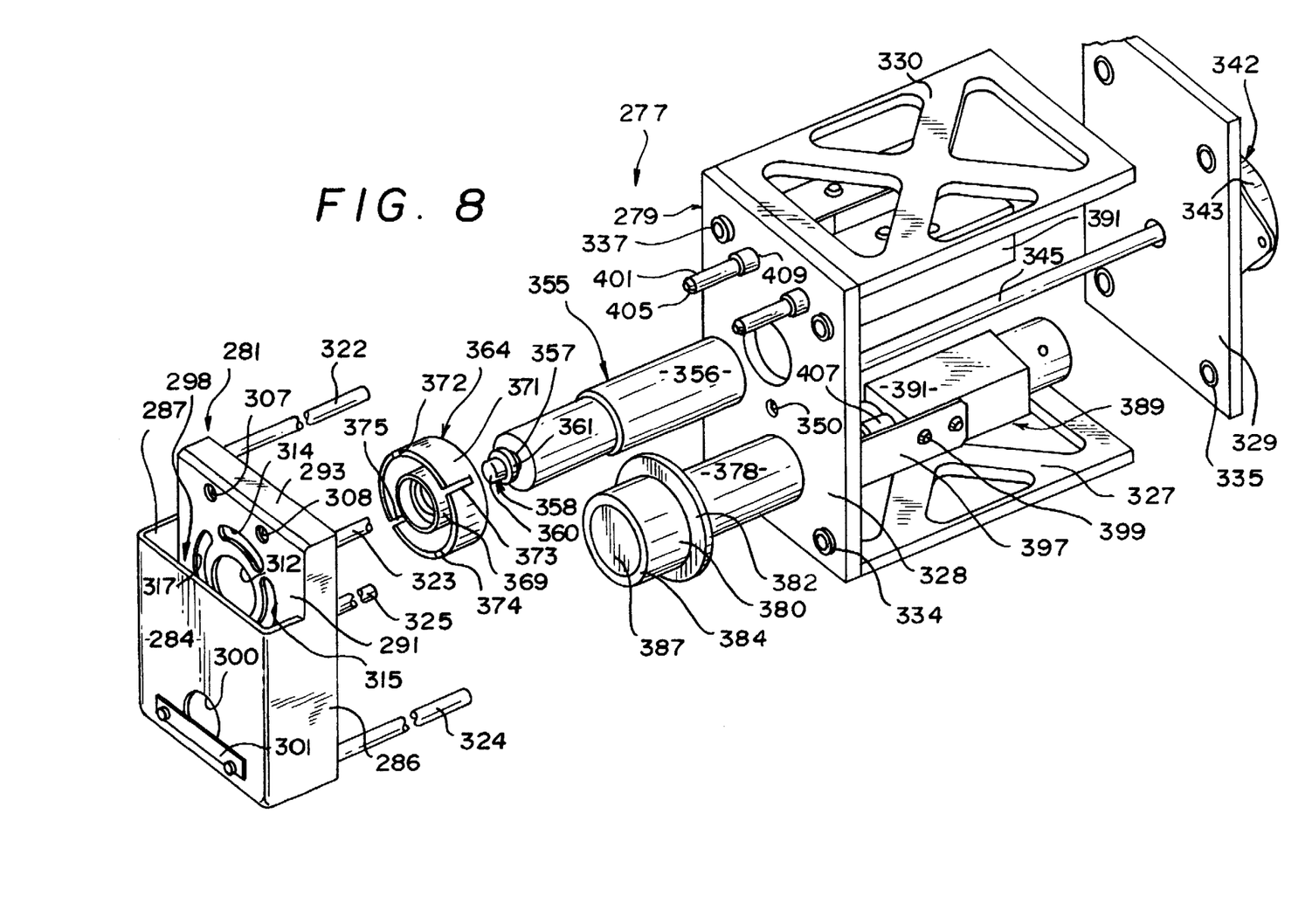
FIG. 8 is an exploded view of a control module incorporated in the present invention.
Figure 10:
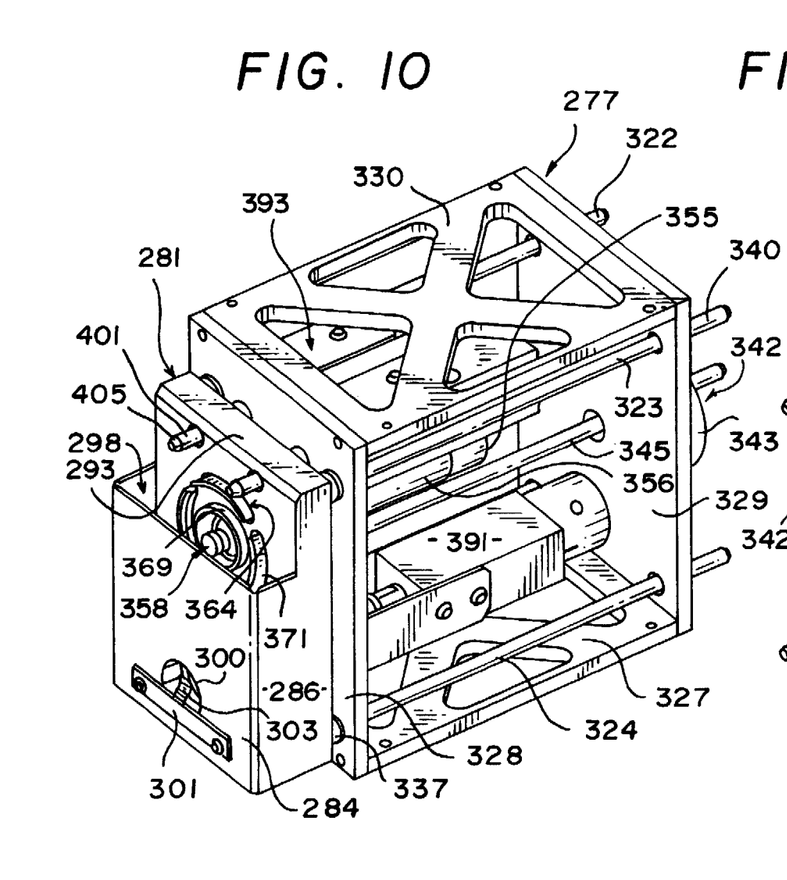
FIG. 10 is a right-side perspective view, similar to that of FIG. 9 but depicting the control module in an in-use position.
Figure 11:
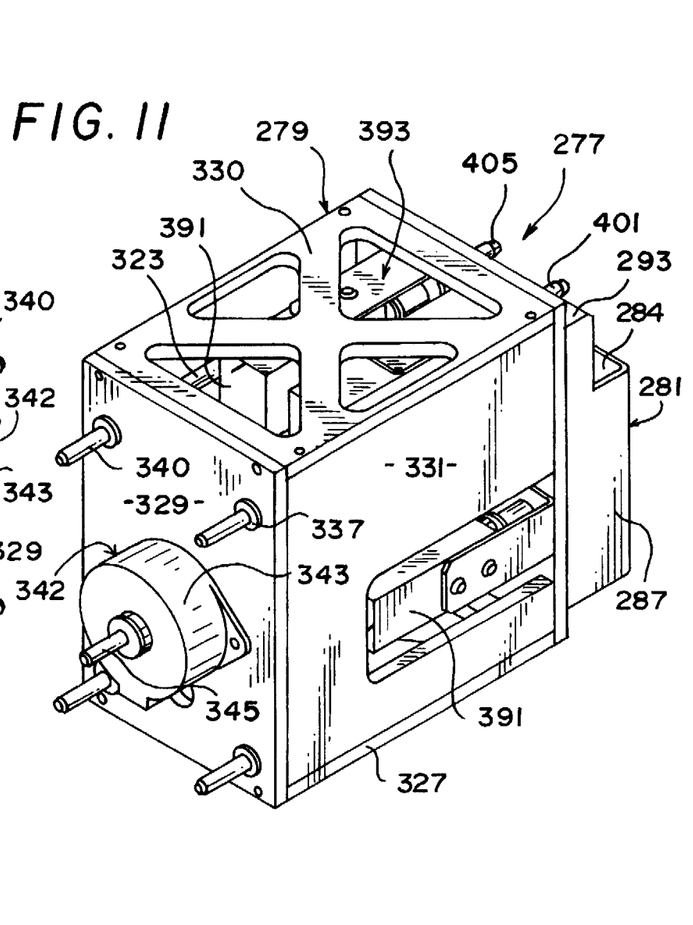
FIG. 11 is a left-rear perspective view of the control module of the invention.
Figure 12:
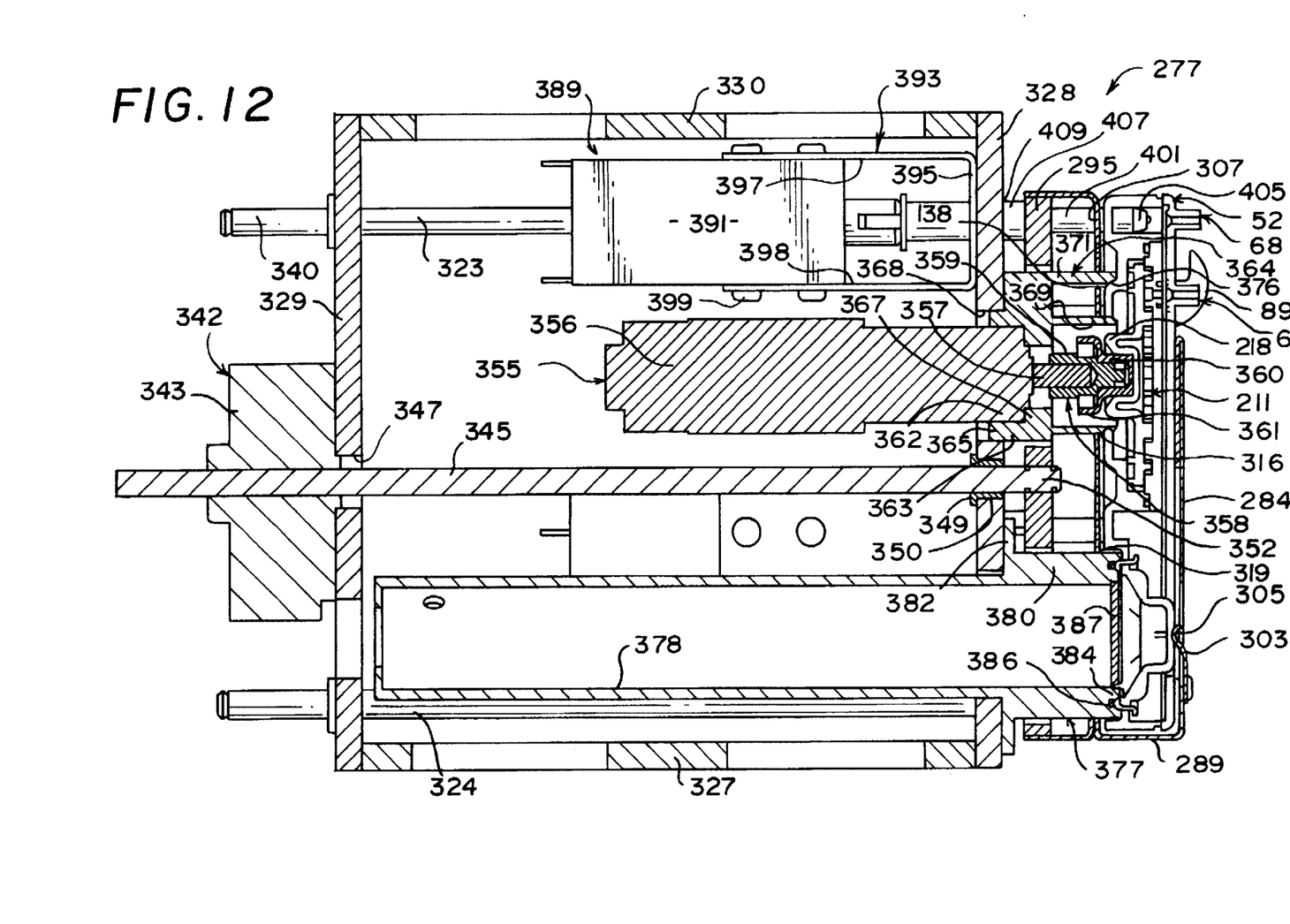
FIG. 12 is a partial cross-sectional, full-sized view of the fluid flow control system of the invention in a loaded and in-use condition.

Reference will now be made to FIGS. 8-12 in describing a control module 277 which cooperates with disposable pump cartridge 52 to define the overall fluid flow control system of the present invention. As shown, control module 277 includes a main body portion 279 and a carrier body portion 281. Carrier body portion 281 includes a front panel 284, side panels 286 and 287, a bottom panel 289, a central panel 291, a top panel portion 293 and a rear plate 295 as best shown in FIGS. 8 and 12. In the preferred embodiment, carrier body portion 281 is made of metal with rear plate 295 being made of aluminum and the remainder of carrier body portion 281 being formed of sheet metal. Between front panel 284 and central panel 291, carrier body portion 281 defines a cartridge receiving area or slot 298 which, as will be discussed more fully below, is adapted to receive disposable cartridge 52. In the preferred embodiment, front panel 284 includes a lower opening 300 across which is positioned a spring member 301 having at least one biasing finger 303 (not shown in FIG. 8 for clarity, but see FIGS. 9, 10 and 12) that has an arcuate terminal end 305. Central panel 291 and rear plate 295 include a pair of aligned and spaced upper apertures 307 and 308. Actually, central panel 291 and rear plate 295 are provided with four such apertures, the other two of which are arranged below central panel 291. The location and purpose of each of these additional apertures will become readily apparent hereinafter.

Central panel 291 is also formed with a central opening 312 about which are spaced a plurality of arcuate slots 314-317. Central panel 291 and rear plate 295 further define a lower rear opening 319 formed in carrier body portion 281. Cantilevered from rear plate 295, generally adjacent the four corners thereof, are respective guide rails 322–325. As will become more clearly evident below, rails 322–325 are slidably supported by main body portion 279 and function to guide carrier body portion 281 during relative shifting movement between carrier body portion 281 and main body portion 279.

Figure 9:
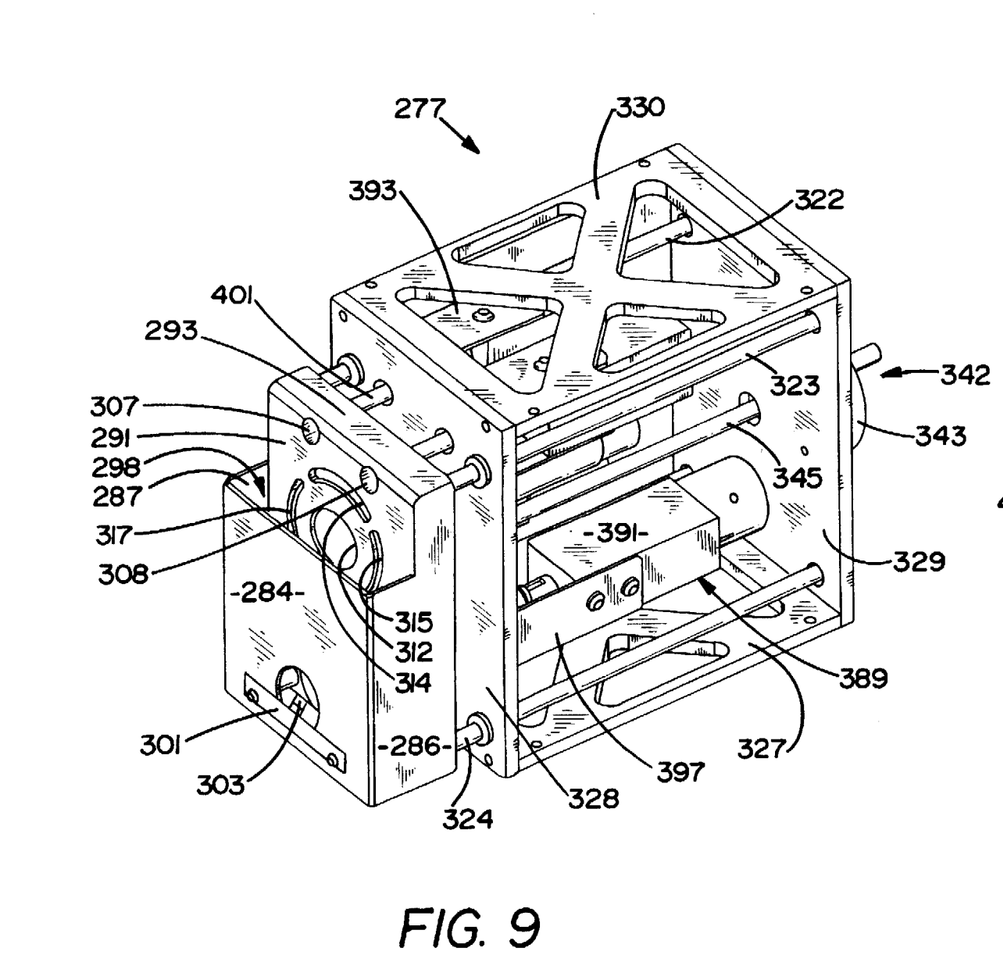
FIG. 9 is a right-side perspective view of the control module in a cartridge loading/unloading position.

In the preferred embodiment shown, main body portion 279 includes a base plate 327, a front plate 328, a rear plate 329, a top plate 330 and at least one side plate 331. In the preferred embodiment, plates 327–331 are formed from aluminum and are interconnected together with conventional mechanical fasteners (not shown). Adjacent each of the corners of front and rear plates 328 and 329 are defined respective front and rear aligned holes 334 and 335 having positioned therein a respective bushing 337 preferably formed of plastic. Within each bushing 337 extends a respective guide rail 322–325. As clearly shown in at least FIGS. 10–12, guide rails 322–325 each include a respective end portion 340 that extends outward beyond rear plate 329. With this arrangement, carrier body portion 281 is slidably supported by main body portion 279 through guide rails 322–325 with carrier body portion 281 being movable towards and away from front plate 328 at least a distance defined by the length of end portions 340. As will be discussed more fully below, movement of carrier body portion 281 relative to main body portion 279 enables carrier body portion 281 to assume an extended, cartridge loading/unloading position as shown in FIG. 9 and an in-use position as shown in FIGS. 10 and 12.

Shifting of carrier body portion 281 relative to main body portion 279 is performed in accordance with the present invention by means of a mechanism generally indicated at 342. Mechanism 342 is preferably constituted by a bi-directional, linear electric motor 343 having an associated longitudinally shiftable shaft 345 that extends through an opening 347 provided in rear plate 329 and a bushing 349 provided in a hole 350 provided in front plate 328. The forward end 352 of shaft 345 is attached, for relative rotation, to rear plate 295 of carrier body portion 281. With this arrangement, activation of linear motor 343 causes shaft 345 to rotate, such as through a helical or worm gear drive, such that shaft 345 is shifted linearly relative to main body portion 279. Since shaft 345 is permitted to rotate relative to rear plate 295, only the longitudinally shifting movement of shaft 345 will be translated to carrier body portion 281. As linear motor 343 can be operated in bi-directionally, carrier body portion 281 can be positively driven between the loading/unloading position and the in-use position. At this point, it should be readily understood that, although mechanism 342 constitutes a linear motor and mechanical drive arrangement in the preferred embodiment, various other types of linear drive systems could be utilized, including solenoid, pneumatic and hydraulic actuators, without departing from the spirit of the invention.

Main body portion 279 also has mounted therein a pump drive motor 355 that includes an encased housing 356 having an output driveshaft 357. As best shown in FIG. 12, output driveshaft 357 has drivingly connected thereto a connector 358 having an inner connector element 359 and an outer connector element 360. Outer connector element 360 includes a flared portion 361. In the preferred embodiment, drive connector 358 actually constitutes an eccentric bushing used to transmit drive to scroll fluid device 211. More specifically, outer connector element 360 is adapted to be received within central hub 218 of first scroll element 214 for driving scroll fluid device 211 upon loading of disposable cartridge 52 in the manner which will be detailed below.

Pump drive motor 355 actually includes a forward housing portion 362 that is mounted to a center section 363 of an alignment bushing 364. Center section of alignment bushing 364 actually includes a first diametric portion 365 and a second, reduced diametric portion 367 and forward end 362 of pump drive motor 355 abuts second, reduced diametric portion 367 and is fixed to first diametric portion 365 as clearly shown in FIG. 12. Alignment bushing 364 itself is fixed in an opening 368 provided in front plate 328. Alignment bushing 364 has a forwardly projecting inner cylindrical sleeve 369 and an outer cylindrical sleeve 371 having various, circumferentially spaced cut-out sections 372–375. Inner cylindrical sleeve 369 is aligned with central opening 312 and the various sections of outer cylindrical sleeve 371 are respectively aligned with arcuate slots 314–317. With this arrangement, when carrier body portion 281 is shifted to its in-use position directly adjacent main body portion 279, inner and outer cylindrical sleeves 369 and 371 project into cartridge receiving area 298. For the reasons which will be more fully discussed below, outer cylindrical sleeve 371 has a tapered front edge 376 as best shown in FIG. 12.

Main body portion 279 also supports a fixed pressure transducer element 377. As best illustrated in FIGS. 8 and 12, fixed pressure transducer element 377 includes a vacuum tube portion 378 having an enlarged diametric head 380 and an annular flange 382. Fixed pressure transducer element 377 is fixedly secured to front plate 328 through annular flange 382 and has a front terminal seat 384 having an O-ring 386 against which pressure transducer element 244 is seated when disposable cartridge 52 is placed within carrier body portion 281 and carrier body portion 281 is moved to its in-use position as shown in FIG. 12. Fixed pressure transducer element 377 further includes a sensing unit indicated at 387 which is adapted to be positioned juxtaposed to diaphragm 249 to sense the deflections of diaphragm 249 based on its exposure to fluid system pressures. Although not shown in these drawings for the sake of clarity, fixed pressure transducer element 377 also incorporates electronic control components within tube 378 to receive signals from sensor unit 387 for use in determining the fluid system pressure in fluid flow circuit 2 based on the sensed movement of diaphragm 249. As indicated above, various different types of known transducer assemblies can be utilized to perform the desired pressure sensing function in accordance with the present invention although the preferred pressure transducer arrangement is disclosed in the above-referenced co-pending U.S. Patent Application that has been incorporated herein by reference.

Main body portion 279 of control module 277 also supports various valve units one of which is generally indicated at 389. In accordance with the preferred embodiment, valve unit 389 constitutes a solenoid valve and therefore includes a solenoid housing 391 which is fixed within main body portion 279 such as through the use of a generally U-shaped bracket 393 that has a base 395 secured to front plate 328 and leg portions 397 and 398 that are attached to solenoid housing 391 by means of a plurality of fasteners 399. Each valve unit 389 includes a linearly shifting valve member 401 in the form of a rod having a tapering tip 405. Each valve member 401 is slidably mounted within a guide sleeve 407 that extends through a respective bore 409 formed in front plate 328. Actually, in the preferred embodiment, four such solenoid valve units 389 are provided, each of which has an associated valve member 401 extending through front plate 328 and which can be linearly shifted. The tapered tip 405 of each valve member 401 is adapted to extend through a respective one of the apertures discussed above with reference to apertures 307 and 308 formed in carrier body portion 281 and then into disposable cartridge 52 at apertures 147–150 respectively. When carrier body portion 281 is in the in-use position, tapered tips 405 can engage elastomeric sheet 177 at first, second, third and fourth valve control points 10, 24, 29 and 49 respectively. Additional details regarding the operation of each valve unit 389 will now be discussed in describing the manner in which the fluid flow control system of the present invention operates.

When preparing for a surgical procedure, control module 277 would initially assume the loading/unloading position illustrated in FIG. 9. Of course, main body portion 279 would have some sort of outer covering which is not shown in order to detail the internal structure of control module 277. In any event, in this position, carrier body portion 281 is spaced from main body portion 279 yet supported through guide rails 322–325. In this position, alignment bushing 364 and the valve member 104 of each valve unit 389 is clear of cartridge receiving area 298. As mentioned above, carrier body portion 281 can be shifted to this loading/unloading position by means of linear motor 343 and the connection of shaft 345 to rear plate 295. As clearly shown, drive connector 358 is also spaced from cartridge receiving area 298. At this point, a new disposable cartridge 52 can be readily placed within cartridge receiving area 298 with central locating projection 252 of pressure transducer element 244 being positioned against finger 303 of spring member 301 and external connection ports 66–69 extending above front panel 284 of carrier body portion 281. In the preferred set-up sequence, a reservoir bag would be attached to disposable cartridge 52 at suspension members 88 and 89, as well as to fourth connection port 69, prior to insertion of disposable cartridge 52 within cartridge receiving area 298. However, the reservoir assembly could equally be attached anytime prior to system start-up.

Once disposable cartridge 52 is in place, an operator would press a button (not shown) which actuates linear motor 343 and causes carrier body portion 281 to be drawn towards main body portion 279 such that control module 277 assumes the in-use position (shown in FIGS. 10 and 11 without cartridge 52 and in FIG. 12 with cartridge 52 in place). Alternatively, cartridge 52 could engage a switch when inserted in cartridge receiving area 298 to automatically cause the shifting of carrier body portion 281. When carrier body portion 281 is drawn to main body portion 279, pressure transducer element 244 is automatically seated against O-ring 386 of fixed pressure transducer element 277, drive connector 358 is automatically positioned within central hub 218, inner cylindrical sleeve 369 of alignment bushing 364 is arranged in central opening 312, outer cylindrical sleeve 371 of alignment bushing 364 extends through arcuate slots 314–317 until tapered front edge 376 is positioned against upwardly extending an inwardly tapering wall 138 formed in second housing section 56 of disposable cartridge 52 and each of the valve members 401 extend through rear plate 295 and front panel 284 of carrier body portion 281 and into disposable cartridge 52 through a respective aperture 147–150. Thereafter, connections can be made at external connection ports 66–68 as discussed above.

At this point, the fluid flow control system of the present invention is operational. During the procedure, pump drive motor 355 can be controlled to operate scroll fluid device 211 to create a suction at third connection point 68 through flow passage 262, pressure transducer element 244 and fluid passage 261. Of course, fluid drawn in from the operation of scroll fluid device 211 is directly delivered to reservoir 41 as the output of scroll fluid device 211 is in direct flow communication with external connection port 69 by means of through hole 199 in elastomeric sheet 177. Calibration valve 49 is normally closed which, in the embodiment disclosed, occurs by extending a respective valve member 401 such that the tapered tip 405 thereof pinches elastomeric sheet 177 and causes the same to obstruct flow through fluid passage 263. This type of valve control can also be provided at first, second and third valve control points 10, 24 and 29. When irrigation is desired, flow is readily permitted within flow passage 261 whereby first and second external connection ports 66 and 67 are placed in fluid communication with each other (i.e., fluid is permitted to freely flow between points 264 and 265 as shown in FIG. 7). As vent line 27 is normally closed, the valve member 401 associated with third valve control point 29 is normally, fully extended.

Figure 13:
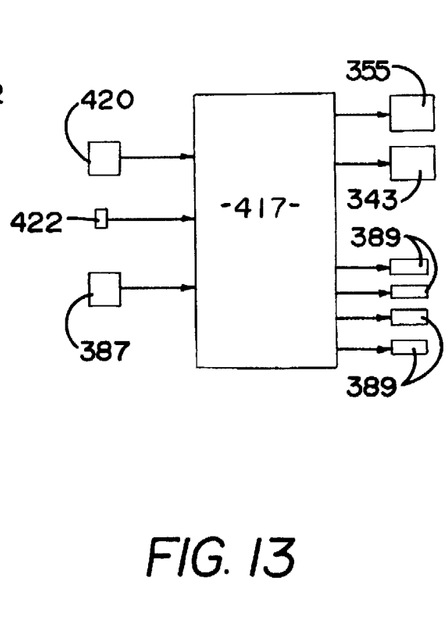
FIG. 13 is a schematic of an electronic control circuit incorporated in the preferred embodiment of the invention.

The operation of pump drive motor 355 and valve units 389 during use of the fluid flow control system of the present invention is actually electronically controlled in accordance with the preferred embodiment. More specifically, as shown in FIG. 13, an electronic control unit 417 is provided which receives inputs from an operator control member (such as a foot pedal) indicated at 420, a manual operating mode control switch 422 and signals from the sensing unit 387. Electronic control unit 417 utilizes these signals to output control signals to each of pump drive motor 355, linear motor 343 and valve units 389. Foot pedal controller 420 is constructed in accordance with those known in the prior art and enables a surgeon to control the irrigation and aspiration as needed. Operating mode control switch 422 can be used to select whether control module 277 provides an established aspiration flow rate, a controlled aspiration vacuum pressure or both. If a flow rate based system is desired, operating mode control switch 422 would be appropriately set and pump drive motor 355 would be accordingly controlled in a manner similar to known peristaltic type systems. On the other hand, operating mode control switch 422 can be positioned in a vacuum-based operating mode wherein electronic control unit 417 would operate pump drive motor 355 based on signals not only received from foot pedal 420 but also from sensing unit 387 associated with fixed pressure transducer element 377. In this mode, control module 277 would function in a manner analogous to known venturi type systems. When operating in a pressure-based mode, electronic control unit 417 would be configured to shut down if an obstruction was presented in the aspiration line which increased system pressure beyond a threshold value. In addition, when operating in a flow rate mode, electronic control unit would also be sensitive to high RPM increases resulting from a possible obstruction in the aspiration line since such a high RPM increase could lead to a surge in the suction after the obstruction is removed. In this mode, electronic control unit 417 would therefore still be sensitive to pressure signals to avoid this potential problematic situation.

Although described with respect to a preferred embodiment of the invention, it should be readily understood that various changes and/or modifications may be made to the invention without departing from the spirit thereof. For example, although the fluid flow control system of the present invention has been described with particular reference in establishing an overall irrigation/aspiration flow control circuit, it should be readily understood that the principles of the present invention could be applied to other fields as well. For example, the system could be used for supplying, removing or recirculating other bodily fluids, or even fields outside the medical environment. In general, the invention is only intended to be limited by the scope of the following claims.

We claim:

1. A fluid flow control system comprising:
    a disposable cartridge including:
        a cartridge housing formed from at least two housing sections which are joined together, said housing sections being provided with at least two fluid connection ports and an opening exposing an interior of said cartridge housing;
        a pump having associated inlet and outlet ports and at least one movable pump element provided with an attachment member adapted to be interconnected with a drive element for operating said pump, said pump being positioned within said cartridge housing with said attachment member being located at said opening; and
        a separating member positioned within said cartridge housing, said separating member defining, at least in part, a plurality of flow passages respectively fluidly interconnected to said at least two fluid connection ports and the inlet and outlet ports of said pump; and
    a control module including:
        a control housing having a main body portion and a carrier body portion, said carrier body portion defining a cartridge receiving area that is adapted to receive said disposable cartridge;
        a drive unit including a drive element adapted to be drivingly connected to the attachment member of said pump following insertion of the disposable cartridge in said cartridge receiving area; and
        means for controlling the operation of said drive unit in order to regulate an operation of said pump.

2. The fluid flow control system according to claim 1, wherein said separating member is constituted by a flexible sheet.

3. The fluid flow control system according to claim 2, wherein said flexible sheet is formed from an elastomeric material.

4. The fluid flow control system according to claim 1, wherein one of said at least two housing sections is formed with a plurality of open channels which are covered by said separating member to define said plurality of flow passages.

5. The fluid flow control system according to claim 4, wherein said separating member is formed with various raised walls which are sealingly mated about said open channels.

6. The fluid flow control system according to claim 1, further comprising a pressure transducer including a disposable transducer element located in said cartridge housing and a re-usable transducer element provided in said control housing, said disposable transducer element being juxtaposed said re-usable transducer element following insertion of the disposable cartridge in said cartridge receiving area.

7. The fluid flow control system according to claim 6, wherein said disposable transducer element includes a fluid inlet that is in fluid communication with at least one of said plurality of flow passages through said separating member.

8. The fluid flow control system according to claim 1, wherein one of said plurality of flow passages interconnects said at least two fluid connection ports to provide for a flow of fluid through said disposable cartridge that is independent of the operation of said pump.

9. The fluid flow control system according to claim 1, wherein said pump constitutes a plastic scroll fluid device.

10. The fluid flow control system according to claim 1, further comprising a plurality of spaced apertures formed in said cartridge housing and a plurality of valve members shiftably mounted on said control housing, each of said valve members being adapted to extend into a respective one of said spaced apertures and to obstruct a flow through a predetermined section of said flow passages.

11. The fluid flow control system according to claim 10, wherein said valve members constitute linear solenoid valve units.

12. The fluid flow control system according to claim 10, wherein said separating member is made from an elastomeric material and each of said valve members is adapted to cause a respective portion of the elastomeric material to project into a predetermined section of the flow passages to thereby obstruct a flow within the flow passages.

13. The fluid flow control system according to claim 1, further comprising a mechanism for shifting said carrier body portion of said control housing between a cartridge loading/unloading position wherein said carrier body portion is spaced from said main body portion and an in-use position wherein said carrier body portion is shifted towards said main body portion.

14. The fluid flow control system according to claim 13, further comprising a plurality of rail members connected to said carrier body portion and slidably received in said main body portion of said control housing, said rail members guiding said carrier body portion for movement between said loading/unloading and in-use positions.

15. The fluid flow control system according to claim 1, wherein said cartridge housing includes a front wall provided with suspension elements adapted to support a reservoir unit, one of said at least two fluid connection ports enabling the reservoir unit to be fluidly connected to said flow passages.

16. A disposable cartridge for use in a fluid flow control system comprising:
    a cartridge housing formed from at least two housing sections which are joined together, said housing sections being provided with at least two fluid connection ports and an opening exposing an interior of said cartridge housing;
    a pump having associated inlet and outlet ports and at least one movable pump element provided with an attachment member adapted to be interconnected with a drive element for operating said pump, said pump being positioned within said cartridge housing with said attachment member being located at said opening; and
    a separating member positioned within said cartridge housing, said separating member defining, at least in part, a plurality of flow passages respectively fluidly interconnected to said at least two fluid connection ports and the inlet and outlet ports of said pump.

17. The disposable cartridge according to claim 16, wherein said separating member is constituted by a flexible sheet.

18. The disposable cartridge according to claim 17, wherein said flexible sheet is formed from an elastomeric material.

19. The disposable cartridge according to claim 16, wherein one of said at least two housing sections is formed with a plurality of open channels which are covered by said separating member to define said plurality of flow passages.

20. The disposable cartridge according to claim 19, wherein said separating member is formed with various raised walls which are sealingly mated about said open channels.

21. The disposable cartridge according to claim 16, further comprising a disposable pressure transducer element located in said cartridge housing.

22. The disposable cartridge according to claim 21, wherein said disposable transducer element includes a fluid inlet that is in fluid communication with at least one of said plurality of flow passages through said separating member.

23. The disposable cartridge according to claim 16, wherein one of said plurality of flow passages interconnects said at least two fluid connection ports to provide for a flow of fluid through said disposable cartridge that is independent of the operation of said pump.

24. The disposable cartridge according to claim 16, wherein said pump constitutes a plastic scroll fluid device.

25. The disposable cartridge according to claim 16, further comprising a plurality of spaced apertures formed in said cartridge housing, each of said spaced apertures being adapted to receive a respective valve member for obstructing a flow through a predetermined section of said flow passages.

26. The disposable cartridge according to claim 16, wherein said cartridge housing includes a front wall provided with suspension elements adapted to support a reservoir unit, one of said at least two fluid connection ports enabling the reservoir unit to be fluidly connected to said flow passages.

27. A fluid flow control system comprising:
   a disposable cartridge including:
      a cartridge housing formed from at least two housing sections which are joined together, said housing sections being provided with at least two fluid connection ports, an internal fluid flow passage circuit fluidly connected to the connection ports and an opening exposing an interior of said cartridge housing; and
      a miniature scroll fluid device formed of plastic, said scroll fluid device having associated inlet and outlet ports in fluid communication with said internal fluid flow passage circuit and at least one movable work element provided with an attachment member adapted to be interconnected with a drive element for operating said scroll fluid device, said scroll fluid device being positioned within said cartridge housing with said attachment member being located at said opening; and
   a control module including:
      a control housing having a main body portion and a carrier body portion, said carrier body portion defining a cartridge receiving area that is adapted to receive said disposable cartridge;
      a drive unit including a drive element adapted to be drivingly connected to the attachment member of said scroll fluid device following insertion of the disposable cartridge in said cartridge receiving area; and
      means for controlling the operation of said drive unit in order to regulate an operation of said scroll fluid device.

28. The fluid flow control system according to claim 27, further comprising a separating member positioned within said cartridge housing, said separating member defining, at least in part, said internal fluid flow passage circuit.

29. The fluid flow control system according to claim 28, wherein said separating member comprises an elastomeric sheet.

30. The fluid flow control system according to claim 29, wherein one of said at least two housing sections is formed with a plurality of open channels which are covered by said separating member to define said internal fluid flow passage circuit.

31. The fluid flow control system according to claim 27, further comprising a plurality of spaced apertures formed in said cartridge housing and a plurality of valve members shiftably mounted on said control housing, each of said valve members being adapted to extend into a respective one of said spaced apertures and to selectively obstruct a flow through a predetermined section of said internal fluid flow passage circuit.

32. The fluid flow control system according to claim 27, wherein said internal fluid flow passage circuit interconnects said at least two fluid connection ports to provide for a flow of fluid through said disposable cartridge that is independent of the operation of said scroll fluid device.

33. The fluid flow control system according to claim 27, further comprising a pressure transducer including a disposable transducer element located in the cartridge housing in fluid communication with said internal fluid flow passage circuit and a re-usable transducer element provided in said control housing, said disposable transducer element being juxtaposed said re-usable transducer element following insertion of the disposable cartridge in said cartridge receiving area.

34. The fluid flow control system according to claim 27, further comprising a mechanism for shifting said carrier body portion of said control housing between a cartridge loading/unloading position wherein said carrier body is spaced from said main body portion and an in-use position wherein said carrier body portion is shifted towards said main body portion.

35. The fluid flow control system according to claim 27, wherein said cartridge housing includes a front wall provided with suspension elements adapted to support a reservoir unit, one of said at least two fluid connection ports enabling the reservoir unit to be fluidly connected to said internal fluid flow passage circuit.

36. A disposable cartridge for use in a fluid flow control system comprising:
   a cartridge housing formed from at least two housing sections which are joined together, said housing sections being provided with at least two fluid connection ports, an internal fluid flow passage circuit fluidly connected to the connection ports and an opening exposing an interior of said cartridge housing; and
   a miniature scroll fluid device formed of plastic, said scroll fluid device having associated inlet and outlet ports in fluid communication with said internal fluid flow passage circuit and at least one movable work element provided with an attachment member adapted to be interconnected with a drive element for operating said scroll fluid device, said scroll fluid device being positioned within said cartridge housing with said attachment member being located at said opening.

37. The disposable cartridge according to claim 36, further comprising a separating member positioned within said cartridge housing, said separating member defining, at least in part, said internal fluid flow passage circuit.

38. The disposable cartridge according to claim 37, wherein said separating member comprises an elastomeric sheet.

39. The disposable cartridge according to claim 38, wherein one of said at least two housing sections is formed with a plurality of open channels which are covered by said separating member to define said internal fluid flow passage circuit.

40. The disposable cartridge according to claim 36, further comprising a plurality of spaced apertures formed in said cartridge housing and a plurality of valve members shiftably mounted on said control housing, each of said valve members being adapted to extend into a respective one of said spaced apertures and to selectively obstruct a flow through a predetermined section of said internal fluid flow passage circuit.

41. The disposable cartridge according to claim 36, wherein said internal fluid flow passage circuit interconnects said at least two fluid connection ports to provide for a flow of fluid through said disposable cartridge that is independent of the operation of said scroll fluid device.

42. The disposable cartridge according to claim 36, further comprising a disposable transducer element located in said cartridge housing in fluid communication with said internal fluid flow passage circuit.

43. The disposable cartridge according to claim 36, wherein said cartridge housing includes a front wall provided with suspension elements adapted to support a reservoir unit, one of said at least two fluid connection ports enabling the reservoir unit to be fluidly connected to said internal fluid flow passage circuit.

44. A method of establishing a fluid flow control system comprising:

inserting a cartridge, containing a pump and defining a plurality of fluid flow passages therein, into a carrier body portion of a control module; and shifting the carrier body portion towards a main body portion of the control module to enable a driveshaft, supported by the main body portion, to be drivingly connected to the pump.

45. The method according to claim 44, further comprising: linearly extending a valve member, supported by the main body portion of the control module, within the cartridge to a fluid flow controlling position with respect to one of said fluid flow passages.

46. The method according to claim 44, further comprising:

sensing a fluid pressure within the fluid flow control system; and selectively setting an operational mode for the fluid flow system such that said pump is driven based on one of a desired fluid flow rate and a desired system pressure.

* * * * *